United States Patent [19]

Toyama et al.

[11] Patent Number: 4,460,693
[45] Date of Patent: Jul. 17, 1984

[54] PLASMIDS DERIVED FROM ACTINOMYCETES

[75] Inventors: Hiromi Toyama; Chuhei Nojiri; Takashi Shomura; Yujiro Yamada, all of Kanagawa, Japan

[73] Assignee: Meiji Seika Kaisha Ltd., Tokyo, Japan

[21] Appl. No.: 379,207

[22] Filed: May 17, 1982

[30] Foreign Application Priority Data

May 15, 1981 [JP] Japan .................................. 56-72185

[51] Int. Cl.$^3$ ........................ C12N 1/00; C12N 15/00
[52] U.S. Cl. ................................ 435/317; 435/172.3; 935/29
[58] Field of Search ............................. 435/172, 317

[56] References Cited

PUBLICATIONS

Sakaguchi et al., Molecular Breeding and Genetics of Applied Microorganisms, by Sakaguchi et al., pp. 42–46 (1980).

Primary Examiner—Alvin E. Tanenholtz
Attorney, Agent, or Firm—Sughrue, Mion, Zinn, Macpeak and Seas

[57] ABSTRACT

Essentially pure plasmids derived from Actinomycetes are described which have at least one restriction cleavage site for specific restriction enzyme and have molecular weight of less than $1.0 \times 10^7$.

4 Claims, 5 Drawing Figures

PLASMIDS DERIVED FROM ACTINOMYCETES

FIELD OF THE INVENTION

The present invention relates to novel plasmids and in greater detail to plasmids derived from Actinomycetes.

BACKGROUND OF THE INVENTION

Plasmids which are extrachromosomal elements are useful as vectors for cloning useful genes in recombinant DNA technology.

Up to now, in studies in DNA recombination, *Escherichia coli* and *Bacillus subtilis*, etc. are used as hosts and plasmids derived from ColEl and Staphylococcus are used as vectors. For example, it has been known that Gram positive genetic information is difficult to be expressed in Gram negative bacteria, and it is believed that utilization of hosts and vectors both of which are derived from Actinomycetes is preferred in operations of genetic recombination of genes derived from Actinomycetes. On the other hand, Actinomycetes are important bacteria for producing useful antibiotics and physiologically active substances, and they are highly expected, because there is the possibility of producing novel useful substances by improvement of strains by means of recombinant DNA technology.

Although plasmids derived from Actinomycetes disclosed in Japanese Patent Applications (OPI) 133397/80, 133398/80 and 124799/80, (The term "OPI" as used herein refers to a "published unexamined Japanese patent application."), etc. have been known, they are not always capable of easily utilizing as plasmids because they have a large molecular weight or they comprise restriction enzymes having a plurality of cleavage sites. Thus, the present inventors has accomplished the present invention by isolating plasmids which becomes useful vectors indispensable for recombinant DNA technology of Actinomycetes and clarifying properties thereof.

SUMMARY OF THE INVENTION

Plasmids of the present invention are characterized by that they have at least one restriction cleavage site for specific restriction enzyme and have a molecular weight of less than $1.0 \times 10^7$. Particularly, plasmids named pSF588, pSF765, pSF701-1, pSF619 and pSF689 are preferred.

BRIEF DESCRIPTION OF THE DRAWINGS

In FIG. 2, though the cleavage site of BamHI and that of PstI are shown as the same point, they do not lie one upon another but they are close to each other.

DETAILED DESCRIPTION OF THE INVENTION

Figure 1:
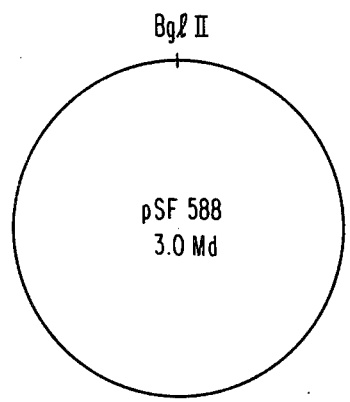
FIG. 1 indicates a restriction enzyme map of plasmid pSF588.
Figure 2:
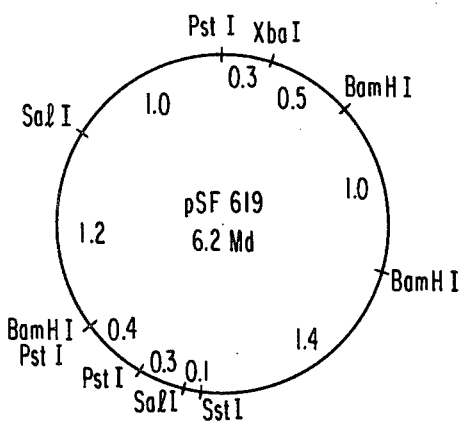
FIG. 2 indicates a restriction enzyme map of plasmid pSF619.
Figure 3:
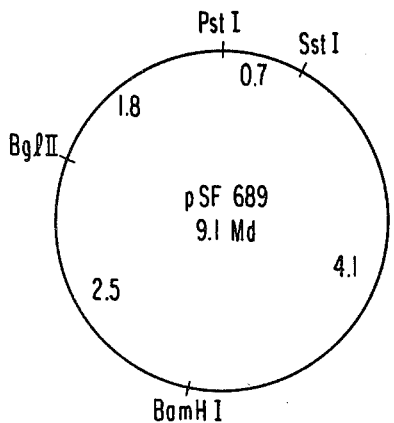
FIG. 3 indicates a restriction enzyme map of pSF689.
Figure 4:
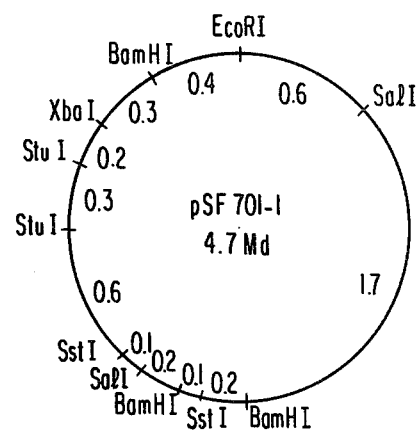
FIG. 4 indicates a restriction enzyme map of plasmid pSF701-1.
Figure 5:
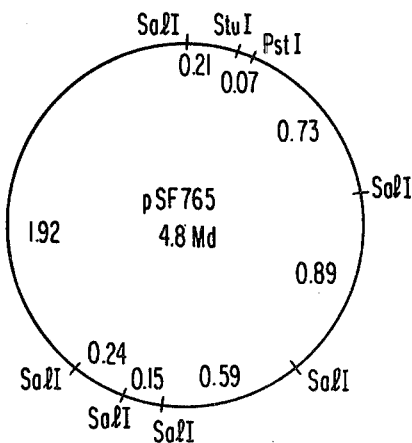
FIG. 5 indicates a restriction enzyme map of pSF765.

Examples of plasmids of the present invention have physicochemical and enzymatic properties as shown in Table 1.

TABLE 1

| | Molecular weight ($\times 10^6$) | | Number of cleavage sites of restriction enzyme | | | | | | | | |
|---|---|---|---|---|---|---|---|---|---|---|---|
| | Enzymatic method (a) | Electron microscopic method (b) | BglII | EcoRI | HindIII | BamHI | SstI | SalI | PstI | XbaI | StuI |
| pSF588 | 3.0 | 3.0 | 1 | 0 | 0 | 0 | 0 | 0 | 0 | 0 | 0 |
| pSF619 | 6.2 | 5.9 | 0 | 0 | 0 | 3 | 1 | 2 | 3 | 1 | 0 |
| pSF689 | 9.1 | 9.2 | 1 | 0 | 0 | 1 | 1 | 5 | 1 | 0 | 0 |
| pSF701-1 | 4.7 | 4.6 | 0 | 1 | 0 | 3 | 2 | 2 | 2 | 1 | 2 |
| pSF765 | 4.8 | 4.4 | 0 | 0 | 0 | 0 | 0 | 6 | 1 | 0 | 1 |

(a) A method which comprises treating the plasmid DNA with a restriction enzyme, analyzing the resulted fragments and calculating the molecular weight (Journal of molecular Biology, 91, 315–328 (1974)).
(b) A method which comprises taking an electron micrograph of a cleavage plasmid, measuring the length thereof, and converting into the molecular weight by calculation (Method in Enzymology, 21d, 413–428 (1971) Academic Press).

Namely, these plasmids have a molecular weight of less than $1.0 \times 10^7$ and have at least on cleavage site for specific restriction enzyme. For example, pSF689 has at least one cleavage site for each of four kinds of restriction enzyme, namely, BglII, BamHI, SstI and PstI.

Further, cleavage maps based on restriction enzymes of these plasmids are as shown in FIGS. 1–5. In the drawings, numerals mean molecular weight by the enzymatic method (unit: Md).

The above described plasmids of the present invention are isolated from the following Actinomycetes, respectively.

pSF588: *Streptomyces albofacients* SF 588, [FERM-P No. 5267 (Nov. 1, 1979), now converted to FERM-BP No. 122 (Apr. 27, 1982)]

pSF619: *Streptomyces hygroscopicus* SF 619, [FERM-P No. 5269 (Nov. 1, 1979), now converted to FERM-BP No. 123 (Apr. 27, 1982)]

pSF689: *Streptomyces platensis* SF 689, [FERM-P No. 5002 (May 25, 1979), now converted to FERM-BP No. 121 (Apr. 27, 1982)]

pSF765: *Streptomyces fradiae* SF 765, [FERM-P No. 5270 (Nov. 1, 1979), now converted to FERM-BP No. 124 (Apr. 27, 1982)]

pSF701-1: *Streptomyces griseochromogens* SF 701, [FERM-P No. 5000 (May 25, 1979), now converted to FERM-BP No. 120 (Apr. 27, 1982)]

Microbial properties of *Streptomyces platensis* SF689 and *Streptomyces griseochromogens* SF701 have been described in detail in Japanese Patent Publications 6878/70 and 6076/70. Properties of other three strains are as follows.

*Streptomyces albofaciens* SF588:

This strain was isolated from a soil in India.

I. Morphological characteristics

Formation of aerial mycelium is generally poor, but good sporulation is observed on sucrose-nitrate agar medium and starch agar medium, etc. Branching is monopodial and verticillate is not observed. Spore-chain is spiral (chiefly, compact spiral). Sclerotium and sporangium are not observed.

When observed by an electron microscope, the surface structure of the spore is smooth. The spores have generally an oval-cyclindric shape having a size of 0.4–0.6×0.6–1.0 microns. Generally, 10 or more of spores are linked to make a chain.

II. Cultural characteristics on various culture media

Cultural characteristics on various culture media at 28° C. for 14–21 days are shown in the following table.

Standards of colors shown in [ ] in the table are those according to classification of Color Harmony Manual (produced by Container Corporation of America).

TABLE

| Medium | Growth and Reverse color | Aerial mycelium | Soluble pigment |
|---|---|---|---|
| Sucrose-nitrate agar | Thin and weak, colorless | White | None |
| Glucose-asparagine agar | Medium, brown | None | None |
| Glycerol-asparagine agar | Weak - medium, colorless - light yellow | Vary poor, white | None |
| Starch agar | Medium, grayish yellow | White | None |
| Oatmeal agar | Medium - good, grayish yellow | None | None or slightly yellow |
| Yeast malt agar | Good, light brownish yellow | Very poor, white | None |
| Tyrosine agar | Medium, light yellow | None | None |
| Nutrient agar | Medium - good, creasy, grayish yellow | poor, white | None |

III. Physiological properties (1) Temperature range for growth: Growth is observed in a temperature range of 15° to 45° C., and good growth is observed at 25°–40° C.

(2) Liquefaction of gelatin: Positive (culture at 20° C. for 21 days.)

(3) Hydrolysis of starch: Positive (culture at 28° C. for 14 days).

(4) Reduction of nitrate: Positive (culture at 28° C. for 14 days).

(5) Peptonization of skim milk: Positive (28° C., 37° C.).

(6) Coagulation of skim milk: Negative (28° C., 37° C.).

(7) Formation of melanoid pigment: Negative.

(8) Antibiotics produced: Oxytetracycline.

IV. Utilization of carbon source (using an agar medium of Pridham and Gottlieb)

(1) Utilization ... D-glucose, D-fructose, D-mannitol, i-inositol and raffinose.

(2) Doubtful utilization ... L-arabionose and L-rhamnose.

(3) No utilization ... D-xylose and sucrose.

V. Composition of cell wall

As a result of analysis by a Becker's method (refer to Appl. Microbiol. 13: 236 (1965)), diaminopimelic acid in components of the cell wall was LL isomer.

Thus, microbial characteristics of the strain SF-588 are summarized as follows. Namely, the spore-chain is spiral and the surface structure of spores is smooth. The aerial mycelium is white and the reverse is grayish white-brown. Special colors are not observed. With respect to soluble pigments, pale yellow color is observed on the oatmeal agar medium, but soluble pigments are not formed in other culture media used. The cell wall contains LL-diaminopimelic acid.

According to the above described microbial properties, the strain SF-588 belongs to the genus Streptomyces and, particularly, it is similar to *Streptomyces albofaciens*. When *Streptomyces albofaciens* according to the description of ISP (International Streptomyces Project) (refer to International Journal of Systematic Bacteriology 18: 287–288 (1968)) and the strain SF-588 are compared, though they are different in utilization of L-arabinose, they well agree with each other in morphological characteristics and culture properties. Further, the strain SF-588 produced oxytetracycline, while it has been known that *Streptomyces albofaciens* produces oxytetracycline, too. (refer to M. J. Thirumalachar et al: Hindustan Antibiot. Bull. 3: 61–63 (1960)). Accordingly, both of them well agree each other with respect to produced antibiotics.

Accordingly, it is reasonable to consider that the strain SF-588 belongs to the species *Streptomyces albofaciens*, because they well agree each other in essential properties though there are some differences in detail. Therefore, the strain SF-588 has been named *Streptomyces albofaciens* SF-588 by the present inventors.

*Streptomyces hygroscopicus* SF 619:

This strain was isolated from soil of a bamboo thicket in Kasaoka City, Okayama Prefecture, Japan.

I. Morphological characteristics

Formation of aerial mycelium is abundant on starch agar medium and yeast malt agar medium, etc. and formation of spores is good. Branching is monopodial and verticillate is not observed. Spore-chain is spiral (chiefly compact spiral). In the latter period of culture (culture for 14–20 days), wet black parts (the so-called hygroscopic area) appear on the aerial mycelium. Sclerotium and sporangium are not observed.

When observed by an electron microscope, the surface structure of the spore is smooth. The spores have generally an oval shape having a size of 0.5–0.8×0-.7–1.0 microns. Generally, 10 or more of spores are linked to make a chain.

II. Cultural characteristics on various culture media

Cultural characteristic on various media at 28° C. for 14–21 days are shown in the following table.

Standards of colors shown in [ ] in the table are those according to classification of Color Harmony Manual (produced by Container Corporation of America).

Appearance of hygroscopic areas is remarkably observed on starch agar medium, oatmeal agar medium and yeast malt agar medium.

TABLE

| Medium | Growth and Reverse color | Aerial mycelium | Soluble pigment |
|---|---|---|---|
| Sucrose-nitrate agar | Weak, colorless | Poor, brownish gray | None |
| Glucose-asparagine agar | Weak, colorless - light yellow | Very poor, white | None |
| Glycerol-asparagine agar | Weak, colorless - light yellow | Poor, white | None |
| Starch agar | Good, grayish yellow | Abundant, brownish gray [2fe] | None |

TABLE-continued

| Medium | Growth and Reverse color | Aerial mycelium | Soluble pigment |
|---|---|---|---|
| Oatmeal agar | Medium - good, grayish yellow tinged with an olive color | Abundant, brownish gray [2fe - 3ig] | None |
| Yeast malt agar | Good, light brown | Abundant brownish gray [2fe - 2ge] | None |
| Tyrosine agar | Weak, light yellow | Poor, white | None |
| Nutrient agar | Weak, light yellow | Poor, white | None |

(1) Temperature range for growth: Growth is observed in a temperature range of 15°–40° C., and good growth is oberved at 26°–37° C.

(2) Liquefaction of gelatin: Positive (culture at 20° C. for 14 days).

(3) Hydrolysis of starch: Positive (culture at 28° C. for 14 days).

(4) Reduction of nitrate: Negative (culture at 28° C. for 14 days).

(5) Peptonization of skim milk: Positive (28° C., 37° C.).

(6) Coagulation of skim milk: Negative (28° C., 37° C.).

(7) Formation of melanoid pigments: Negative.

(8) Antibiotic produced: Paromomycin.

IV. Utilization of carbon source (using an agar medium of Pridham and Gottlieb)

(1) Utilization . . . D-glucose, D-fructose, D-mannitol, i-inositol, raffinose and D-xylose.

(2) No utilization . . . L-arabinose, L-rhamnose and sucrose.

V. Composition of cell wall

As a result of analysis by a Becker's method (refer to Appl. Microbiol. 13: 236 (1965)), diaminopimelic acid in components of the cell wall was LL isomer.

Thus, microbial characteristics of the strain SF-619 are summarized as follows. Namely, spore-chain is spiral, and the surface structure of the spore is smooth. The aerial mycelium has a color of brownish gray, and hygroscopic areas appear in the latter period of culture. The reverse color is light yellow-grayish yellow and special colors are not observed. Soluble pigments are not formed in all culture media used. The cell wall contains LL-diaminopimelic acid.

According to the above described microbial properties, the strain SF-619 belongs to the genus Streptmyces, among which, *Streptmyces hygroscopicus* seems most clearly related. Namely, essential characteristics of *Streptmyces hygroscopicus* such as (1) appearance of hydroscopic area, (2) formation of brownish gray aerial mycelium, (3) spiral spore-chain and (4) no formation of melanine pigments are observed in the strain SF-619.

Accordingly, it is reasonable to consider that the strain SF-619 belongs to the species *Streptomyces hydrgoscopicus*. Thus, the strain SF-619 has been named *Streptomyces hygroscopicus* SF-619 by the present inventors.

*Streptomyces fradiae* SF 765:

This strain was isolated from a soil in Minamiitabashi, Tokyo, Japan.

I. Morphological characteristics

Formation of aerial mycelium is abundant on starch agar medium, oatmeal agar medium and tyrosine agar medium, etc. and formation of spores is good. Branching is monopodial and verticillate is not observed. Spore-chains are various shapes including straight, wave, loop, hook, primitive spiral and true spiral. Sclerotium and sporangium are not observed.

When observed by an electron microscope, the surface structure of the spores is smooth. The spores have generally an oval-cylindric shape having a size of 0.6–0.9×0.8–1.4 microns. Spore-chains are generally short, sometimes with less than 10 spores per chain.

II. Cultural characteristics on various culture media

Cultural characteristics on various media at 28° C. for 14–21 days is shown in the following table.

Standards of colors shown in [ ] in the table are those according to classification of Color Harmony Manual (produced by Container Corporation of America).

TABLE

| Medium | Growth and Reverse color | Aerial mycelium | Soluble pigment |
|---|---|---|---|
| Sucrose-nitrate agar | Weak, colorless | Poor, light pink [5ca] | None |
| Glucose-asparagine agar | Very weak, colorless | None | None |
| Glycerol-asparagine agar | Weak, colorless | Light pink [5ca] | None |
| Starch agar | Good, grayish yellow - grayish orange | Abundant, grayish pink [5ec - 5gc] | None |
| Oatmeal agar | Good, grayish yellow | Abundant, light rose beige [4ec - 5gc] | None |
| Yeast malt agar | Medium - good, brownish yellow | Pinkish gray [5gc] | None |
| Tyrosine agar | Medium, light grayish yellow | Abundant, pinkish brown [5gc] | None |
| Nutrient agar | Medium, light yellow | Poor, light pink [5ca] | None |

III. Physiological properties (1) Temperature range for growth: Growth is observed in a temperature range of 15°–40° C., and good growth is observed at 26°–32° C.

(2) Liquefaction of gelatin: Positive (culture at 20° C. for 21 days).

(3) Hydrolysis of starch: Positive (culture at 28° C. for 14 days).

(4) Reduction of nitrate: Positive (culture at 28° C. for 14 days).

(5) Peptonization of skim milk: Positive (culture at 28° C. for 14 days).

(6) Coagulation of skim milk: Negative (28° C., 37° C.).

(7) Formation of skim milk: Negative.

(8) Antibiotic produced: Neomycin.

IV. Utilization of carbon source (using an agar medium of Pridham and Gottlieb)

(1) Utilization . . . D-glucose, D-fructose, D-xylose and L-arabinose.

(2) No utilization . . . D-mannitol, i-inositol, L-rhamnose, raffinose and sucrose.

V. Composition of cell wall

As a result of analysis by a Becker's method (refer to Appl. Microbiol 13: 236 (1965)), diaminopimelic acid in components of the cell wall as LL-isomer.

Thus, microbial characteristics of the strain SF-765 are summarized as follows. Namely, spore-chains are various shapes including straight to spiral, and the surface structure of spores is smooth. The aerial mycelium has a color of grayish pink-brownish pink, and the reverse has a color of grayish yellow-brownish yellow. Soluble pigments are not formed in all culture media used. The cell wall contains LL-diaminopimelic acid.

According to the above described microbial properties, the strain SF-765 belongs to the genus Streptomyces, among which, *Streptomyces fradiae* seems most closely related. When *Streptomyces fradiae* according to the description of ISP (International Streptomyces Project) (refer to International Journal of Systematic Bacteriology 18: 118-120 (1968)) and the strain SF-765 are compared, both of them agree very well with respect to all of morophological characteristics, culture properties and utilization of carbon source. Further, since both *Streptomyces fradiae* and the strain SF-765 produce neomycin, they agree with each other with respect to produced antibiotic.

Accordingly, it is reasonable that the strain SF-765 belongs to the species *Streptomyces fradiae*. Thus, the strain SF-765 has been named *Streptomyces fradiae* SF-765 by the present inventors.

Isolation of plasmids of the present invention from Actinomycetes and purification thereof are carried out according to the process described in Journal of Antibiotics; vol. 33, pages 118-121 (1980). However, the concentration of glycine in case of incubating Actinomycetes are 2.0%, 0.5%, 0.5%, 0.5% and 0.5%, respectively, for *Streptomyces albofaciens* SF 588, *Streptomyces hygroscopicus* SF 619, *Streptomyces platensis* SF 689, *Streptomyces fradiae* SF 765 and *Streptomyces griseochromogens* SF 701.

The molecular weight of purified plasmids is determind by preparing a sample according to the method by Davis et al (Methods in Enzymology; vol. 21, pages 413-428 (1971), Academic Press, New York and London), taking an electron microphotograph of open circular DNA molecules, measuring the length thereof by a curvimeter, and calculating with a conversion rate of 1 $\mu m = 2 \times 10^6$ daltons.

Restriction enzymes used for the treatment and analysis of the resulted fragments are Eco RI, Hind III, Bam HI, Pst I, Bgl II and Sal I (produced by Miles Lab. Co.), Sst I and Xba I (produced by Bethesda Res. Lab. Inc.) and Stu I (produced by Wako Pure Chemical Ltd.), which are available in the market.

For restriction enzymatic digestion, DNA was treated with at least three time excess amount of restriction enzymes under the conditions according to the supplier's direction.

Further, in case of treating the plasmid with two or more restriction enzymes, if the composition of the reacting solutions is common each other, reactions are carried out at the same time. If the composition of the reacting solutions is different each other, the reaction under a low salt condition is previously carried out and thereafter the salt concentration is increased to make an optimum reacting condition, followed by adding the other enzymes to carry out the reaction. Namely, after the first enzyme treatment, the enzyme is inactivated by heating to 60° C. for 10 minutes. After cooled, proteins were removed by a phenol SDS procedure, followed by dialysis. Then the reacting composition is controlled and the second enzyme treatment and then the third enzyme treatment are carried out. Analysis by agarose gel electrophoresis is carried out according to the method described in Method in Molecular Biology, vol. 7, 87 (1974).

As described above, plasmids of the present invention have a low molecular weight and have at least one cleavage site for specific restriction enzyme, and isolation and purification thereof are easily carried out. Accordingly, they are noted as useful vectors for recombinant DNA technology.

Recombinant plasmid DNA can be produced by known manner. For example, pSF701-1 is cleaved with EcoRi or XbaI to form a linear DNA. On the other hand, other non-vector DNA molecules can be cleaved with the same enzyme. When the resulted linear DAN molecule and the non-vector DAN are mixed, the ends of a single chain of them make a pair each other. Thereafter, polynucleotide ligase is added, by which both of them are combined by covalent bonds to form a circular DNA molecule.

Using the resulted recombinant plasmid, cloning of the non-vector DNA can be carried out by transformation of a suitable host cell. For example, the method of transformation in Actinomycetes and cloning of a neomycin-resistant gene from *Streptomyces fradiae* have been reported in Nature, 274, 398-400 (1978) and Nature 286, 525-529 (1980), etc.

Further, the plasmids of the present invention except for pSF588 are capable of making smaller-sized plasmids which can be easily utilized, because they have a plurality of restriction enzyme cleavage sites. Moreover, it is possible to prepare shuttle vectors (plasmids capable of multiplying by any different host) for example, shuttle vectors made of plasmids of the present invention and *Escherichia coli* vector, pBR322, or Bacillus subtilis vector, pUB110, etc.

In the following, the present invention is illustrated in greater detail with reference to Examples and Reference Examples. Unless otherwise indicated, all percents are percent by weight per volume (w/v).

EXAMPLE 1

Isolation of plasmid pSF588 from *Streptomyces albofaciens* and purification thereof:

Slant cultured or freeze-dried cells of *Streptomyces albofaciens* SF 588 were inoculated into 20 ml of a MYG medium (1% of malt extract (produced by Difco Labs), 0.4% of yeast extract (produced by Difco Labs) and 2% of glucose, pH: 7.0) and incubated at 28° C. for 2 days with shaking at 120 r.p.m. Thereafter, 2 ml of seed culture was inoculated to 80 ml fresh MYG medium containing 2% glycine, and inculated at 28° C. for 2 days with shaking at 120 r.p.m. After incubation, the mycelia were harvested, and washed twice with a 20 mM Tris HCl buffer containing 0.14M sodium chloride (pH 8.0). The resulted mycelia were suspended in 5 ml TE sucrose buffer (0.1M Tris HCl, 0.02M EDTA and 25% sucrose, pH 8.0) per 1 gram of the wet mycelia. 0.1 ml of RNase (produced by Sigma Co., which was prepared by dissolving 5 mg/ml in a 0.85% solution of sodium chloride and treated at 80° C. for 15 minutes) and 0.1 ml of 30 mg/ml lysozyme (produced by Sigma Co.) were added thereto and the reaction was carried out at 37° C. for about one hour. The reaction mixture was cooled to 0° C., 6 ml of sterilized water and 0.25 ml of 5% sodium dodecylsulfate were added and the mixture was mixed gently in an ice bath for 5 minutes to carry out complete lysis. Thereafter, 3.1 ml of aqueous solution of sodium chloride (5M) was added, and the mixture was allowed to stand at 0°-4° C. overnight. A cleared lysate was obtained by centrifugation at 10,000 g for 60 minutes. To this lysate, polyethylene glycol 1000 was added so as to result in the final concentration of 10%. After the lysate was kept at 0° C. for 4 hours, it was centrifuged at 10,000 g for 10 minutes to obtain a precipitate. The resulted precipitate was dissolved in a sarcosyl-TE buffer (10 mM Tris HCl, 10 mM EDTA and 0.4% sodium lauroyl sarcosinate, pH 8.0) and the whole amount was adjusted to 4.76 ml with the same buffer solution. To the resulted solution, 5 g of cesium chloride was added to dissolve therein, and 0.5 ml of 4.7 mg/ml ethidium bromide solution was added. The mixture was put in a centrifuge tube made of nitrocellulose, CsCl-ethidium bromide boyant density gradient centrifugal separation was carried out at 20° C. for 40 hours or more at 36,000 r.p.m. on a Beckman model L2-75B ultracentrifuge in a 75 Ti fixed angle rotor. The centrifuging tube was irradiated with 365 nm ultraviolet and a band of plasmid DNA was taken out as a plasmid fraction.

Further, after removing ethidium bromide with n-butanol extraction, the plasmid DNA was dialyzed against TE buffer (10 mM Tris HCl buffer and 1 mM EDTA, pH 8.0). Purification of the sample after dialysis was carried out by 5-20% neutral sucrose density gradients centrifugation. Namely, using a TEN buffer containing ethidium bromide (10 mM Tris HCl buffer solution, 20 mM EDTA, 50 mM sodium chloride and 1 μg/ml ethidium bromide, pH 8.0), a mixture of 0.5 ml of the sample and 0.05 ml of ethidium bromide (5 mg/ml) was superposed on a 5-20% sucrose linear density gradients, and centrifugal separation was carried out at 4° C. for 3 hours at 40,000 r.p.m. on a Beckman model L2-75B ultracentrifuge in a SW 40 rotor. This centrifuge tube was irradiated with 365 nm ultraviolet, and a plasmid band emitting fluorescence was taken out. After removing ethidium bromide with n-butanol extraction, the pSF588 plasmid DNA was dialyzed against a TE buffer to obtain a purified plasmid.

In order to determine the molecular weight, first, an electron microscopic method was used, which comprises taking an electron micrograph of open circular DNAs by a method by Davis, et al (above described), measuring the contour length thereof by a curvi meter, and calculating by a conversion rate of 1 μm = $2 \times 10^6$ daltons.

Determination of the molecular weight by an enzymatic method was carried out by an agarose electrophoresis method after subjected to restriction enzyme treatment of the plasmid. Namely, the molecular weight of a linear DNA fragment obtained by the restriction enzyme digestion of the plasmid was calculated by measuring a relative mobility to Hind III digests of λ phage DNA or a Hind III digests of SV40 DNA by the agarose electrophoresis method. In case of having a plurality of fragments, it was calculated as the sum total. Molecular weights are shown in Table 1.

Restriction enzyme maps were constructed as follows. 0.5-1 μg of plasmid DNA was allowed to react with 9 kinds of restriction enzymes (Bgl II, EcoRI, Hind III, BamHI, Sst I, Sal I, Pst I, Xba I and Stu I) in an amount of 5 units, respectively, under an optimum reacting condition of each restriction enzyme at 37° C. for 2 hours. A reaction stopping solution (5% sodium dodecylsulfate, 25% glycerol and 0.025% Bromophenol Blue) in an amount of 1/10 of said reaction mixture was added thereto. After carried out the treatment at 65° C. for 10 minutes, it was rapidly cooled. Then, analysis was carried out by agarose gel electrophoresis. Namely, using a 0.8% agarose gel, electrophoresis was carried out in a Tris boric acid buffer solution (89 mM Tris buffer solution, 2.5 mM EDTA and 89 mM boric acid). The gel was then dyed by dipping in 1 μg/ml of a solution of ethidium bromide. The resulted gel was irradiated with 365 nm ultraviolet to take a photograph of bands emitting fluorescence. The number of bands were measured to determine the number of cleavage sites of each restriction enzyme in each plasmid. Further, the molecular weight of each fragment was calculated by the known method, and the number of the cleavage sites was examined. In case that the plasmid had a plurality of restriction enzyme cleavage sites, the restriction enzyme map was constructed by measuring a relative distance between restriction enzyme cleavage sites by the known method. (FIG. 1).

EXAMPLE 2

Isolation of a plasmid from *Streptomyces hygroscopicus* SF 619 and purification thereof were carried out by the same procedure as in Example 1, except that the concentration of glycine in medium was varied so as to be 0.5%, to obtain purified plasmid pSF619.

Measurement of the molecular weight and construction of the restriction enzyme map were carried out by the same procedure as in Example 1. Results are shown in Table 1 and FIG. 2.

EXAMPLE 3

Isolation of a plasmid from *Streptomyces platensis* SF 689 and purification thereof were carried out by the same procedure as in Example 1, except that the concentration of glycine in medium was varied so as to be 0.5%, to obtain purified plasmid pSF 689.

Measurement of the molecular weight and construction of the restriction enzyme map were carried out by the same procedure as in Example 1. Results are shown in Table 1 and FIG. 3.

EXAMPLE 4

Isolation of a plasmid from *Streptomyces fradiae* SF 765 and purification thereof was carried out by the same procedure as in Example 1, except that the concentration of glycine in medium was varied so as to be 0.5%, to obtain purified plasmid pSF 765.

Measurement of the molecular weight and construction of the restriction enzyme map were carried out by the same procedure as in Example 1. Results are shown in Table 1 and FIG. 4.

EXAMPLE 5

Since a cell of *Streptomyces griseochromogens* SF 701 comprised two plasmids having each a different molecular weight, preparation was carried out by the same procedure as in Example 1 (except that the concentration of glycine in medium was 0.5%) by CsCl-ethidium bromide boyant density gradient centrifugation, and then separation was carried out by 5-20% neutral sucrose density gradient centrifugation. The centrifuge tube was irradiated with 365 nm ultraviolet, and a plasmid pSF 701-1 having a lower molecular weight which appeared the upper part of the centrifuge tube was taken out. After removing ethidium bromide with n-butanol extraction, the plasmid DNA was dialyzed against TE buffer to obtain purified plasmid pSF 701-1.

Measurement of the molecular weight and production of the restriction enzyme map were carried out by the same procedure as in Example 1. Results are shown in Table 1 and FIG. 5.

REFERENCE EXAMPLE 1

Isolation of strain:

*Streptomyces albofaciens* SF 588, *Streptomyces hygroscopicus* SF 619 and *Streptomyces fradiae* SF 765 were isolated from a soil in India, a soil in a bamboo thicket of Kasaoka City in Okayama Prefecture, and a soil in Minamiitabashi in Tokyo, respectively, by the following method.

4 g of a soil was suspended in 40 ml of sterilized water (using a 100 ml conical flask). After shaked for 10 minutes on a rotary shaker, it was allowed to stand for 15 minutes to precipitate rough heavy soil particles. 4 ml of the supernatant (muddy) was taken out and diluted ten thousandfold with sterilized water. 0.5 ml of the diluted solution was put on a Petri dish, and 20 ml of an agar medium for separation which was sterilized and heated to 45°-50° C. was added thereto. After the diluted solution of the soil and the medium were mixed so as to become homogeneous as far as possible, the mixture was allowed to stand to solidify the agar medium. This Petri dish was incubated at 28° C. for 10 days. A colony of the object strain growing on the agar was inoculated on a slant of yeast-starch agar (0.2% of enzyme extract, 1.0% of soluble starch and 2.0% of agar, pH 7.0).

The agar medium for separation, having the following composition was used.
Enzyme extract: 0.05%,
Soluble starch: 0.25%,
Agar: 2.0%,
Tap water: Balance pH 7.0 (before sterilization).

REFERENCE EXAMPLE 2

Culture of *Streptomyces albofaciens* SF 588 and isolation of oxytetracycline (1) Culture A loopful of the strain *Streptomyces albofaciens SF* 588 (FERM-P No. 5267) sufficiently grown on a sucrose-nitrate agar medium was inoculated into a test tube containing 10 ml of the following speed culture medium and incubated at 28° C. for 20 hours with shaking by means of a tube shaker.
Seed culture medium:
Soluble starch: 2.0%,
Polypeptone: 1.0%.
Meat extract: 0.3%,
$K_2HPO_4$: 0.05%,
Tap water: Balance (pH 7).

1 ml of culture was inoculated into five Sakaguchi flasks each containing 100 ml of the above described culture medium, and incubated at 28° C. for 20 hours with shaking by means of a reciprocal shaker. The culture was used as a second seed culture. The second seed culture was transferred into a 50 liter jar fermenter containing 35 liter of the following production medium, and incubated at 35° C. for 50 hours with stirring under aeration.
Production medium:
Soluble starch: 2.0%,
Soybean powder: 2.5%,
Wheat germ: 1.0%,
NaCl: 0.25%,
Tap Water: Balance (pH 7.0, before sterilization adjusted with NaOH).

After carried out culture, it was filtered to obtain 20 liter of a filtrate.

(2) Isolation of oxytetracycline 20 liter of the culture filtrate was controlled so as to adjust pH 4 with 6N HCl, and 100 g of active charcoal was added thereto, followed by stirring. By this operation, oxytetracycline in the culture filtrate was absorbed on the active charcoal. After stirred for 30 minutes, the active charcoal was collected by filtration and washed with 3 liter of water. The active charcoal was mixed with 10 liter of 50% acetone aqueous solution, and the pH was adjusted to 9 with 5N NaOH with stirring. After further stirred for 40 minutes, it was filtered to obtain 9 liter of a filtrate. It was condensed in vacuum to remove acetone.

4.7 liter of the resulted aqueous solution was allowed to pass through a column packed with 500 ml of cation-exchange resin: Amberlite CG-50 (Type H+) (produced by Rohm and Haas Co., U.S.A.) to adsorb oxytetracycline on the resin. After washed the resin with 1 liter of water, elution was carried out with a 50% aqueous solution of acetone to obtain every 500 ml of fractions. Activity of each fraction was examined by a paper disk method using *Staphylococcus aureus* 209 p as a testing microbe. Fractions having high activity (No. 1-4) were collected (2 liters) and condensed till about 100 ml in vacuum. After the pH of the resulted condensed solution was adjusted to 8 with 5N NaOH, the solution was allowed to stand at 5° C. to precipitate crystals of oxytetracycline. The crystals were filtered off and recrystallized (by dissolving in 1N HCl, removing impurities and adjusting to pH 8) to obtain 85 mg of needle-like crystals of oxytetracycline.

REFERENCE EXAMPLE 3

Culture of *Streptomyces hygroscopicus* SF 619 and isolation of paromomycin I (1) Culture A platinum spoonful amount of the strain *Streptomyces hygroscopicus* SF 619 (FERM-P No. 5269) sufficiently grown on a yeast-starch agar medium (0.2% of enzyme extract, 1.0% of soluble starch and 2.0% of agar, pH 7) was inoculated into test tubes (using five tubes) each containing 10 ml of the following seed medium and incubated at 28° C. for 24 hours with shaking by means of a tube shaker.
Seed medium:
Glucose: 2.0%,
Polypeptone: 1.0%,
Meat extract: 0.3%,
NaCl: 0.05%,
Tap water: Balance (pH 7).

0.8 ml of the seed culture was inoculated into Sakaguchi's flasks (using 50 flasks) each containing 80 ml of the following production medium, and incubated at 28° C. for 4 days with shaking by means of a reciprocal shaker.
Production medium:
Soluble starch: 2.0%,
Sucrose: 2.0%,
Soybean powder: 3.0%, Wheat germ: 2.0%,
NaCl: 0.25%,
Tap water: Balance (pH 7.0, adjusted with NaOH before sterilization).
After incubation, it was filtered to obtain 3 liters of a filtrate.

(2) Isolation of paromomycin I 3 liters of the culture filtrate (pH 7.6) was allowed to pass through a column packed with 300 ml of the cation-exchange resin: Amberlite IRC-50 (type $NH_4^+$) (produced by U.S. Rohm and Haas Co.) to adsorb paromomycin in the culture filtrate on the resin. After washed the resin with 1.5 liter of water, elution was carried out with 0.5N $NH_4OH$ to obtain every 150 ml of fractions. Activity of each fraction was examined by a paper disk method using *Bacillus subtilis* ATCC 6633 as a testing microbe. Active fractions (Fraction No. 2 and 3) were collected (300 ml) and condensed in vacuum till 30 ml. The resulted condensed solution was allowed to pass through a column containing 30 ml of the cation-exchange resin: Amberlite CG-50 (type $NH_4^+$) (produced by U.S. Rohm and Haas Co.), washed with 150 ml of water. Thereafter, the resin was washed with 300 ml of 0.15N $NH_4OH$, and elution was carried out with 0.3N $NH_4OH$.

Active fractions were collected (60 ml) and condensed to dryness in vacuum to obtain 180 mg of a crude powder of paromomycin (purity 75%). The resulted crude powder was dissolved in a small amount of water, and chromatographed with water on a column of the anion-exchange resin: Dowex 1×2 (type $OH^-$) (produced by U.S. Dow Chemical Co.) (25 ml). Active fractions were collected and condensed to dryness in vacuum, and 63 mg of free base of paromomycin I was isolated as a white powder.

REFERENCE EXAMPLE 4

Culture of strain *Streptomyces fradiae* SF 765 and isolation of neomycin:

(1) Culture 2-3 loopful of the strain *Streptomyces fradiae* SF 765 (FERM-P No. 5270) sufficiently grown on a yeast-starch agar medium (0.2% of enzyme extract, 1.0% of soluble starch and 2.0% of agar; pH 7) were inoculated into Sakaguchi flasks (using eight flasks) each containing 100 ml of the following speed medium and incubated at 28° C. for 20 hours with shaking by means of a reciprocal shaker. The resulted culture were used as a seed culture.

Seed medium:
  Soluble starch: 2.0%,
  Polypeptone: 1.0%,
  Meat extract: 0.3%,
  $K_2HPO_4$: 0.05%,
  Tap water: Balance (pH 7).

400 ml of the seed culture was transferred into 30 liters jar fermenter sterilized (using two devices) which contained 20 liters of the following production medium, and incubated at 28° C. for 69 hours with stirring under aeration.

Production medium:
  Soluble starch: 2.0%,
  Soybean powder: 2.5%,
  Wheat germ: 1.5%,
  $CaCO_3$: 0.3%,
  Tap water: Balance (pH 7.0, adjusted with NaOH before sterilization).

After incubation, it was filtered to obtaain 27 liters of a filtrate.

(2) Isolation of neomycin (mixture of B and C)

27 liters of the culture filtrate (pH 8.0) was allowed to pass through a column containing 2.5 liters of the cation-exchange resin Amberlite IRC-50 (type $NH_4^+$) (produced by U.S. Rohm and Haas Co.) to adsorb neomycin in the culture filtrate on the resin.

After washed the resin with 12.5 liters of water, elution was carried out to obtain every 1 liter of fractions. Activity of each fractions was examined by a paper disk method using *Bacillus subtilis* ATCC 6633 as a testing microbe. Active fractions (Fraction No. 2-4) were condensed till 150 ml in vacuum. Then, the resulted condensed solution was allowed to pass through a column containing 200 ml of Amberlite CG-50 (type $NH_4^+$) (produced by U.S. Rohm and Haas Co.). After washed with 1 liter of water and then 1 liter of 0.1N $NH_4OH$, elution was carried out with 0.3N $NH_4OH$. Active fractions were condensed to dryness in vacuum to obtain 880 mg of a crude powder of neomycin. The resulted crude powder was dissolved in a small amount of water, and chromatographed with water on a column of 80 ml of Dowex 1×2 (type $OH^-$) (produced by U.S. Dow Chemical Co.). Active fractions were condensed to dryness in vacuum, and 340 mg of free base of neomycin (mixture of B and C) was isolated as a white powder.

While the invention has been described in detail and with reference to specific embodiment thereof, it will be apparent to one skilled in the art that various changes and modifications can be made therein without departing from the spirit and scope thereof.

What is claimed is:

1. An isolated essentially pure plasmid derived from Actinomycetes having at least one restriction cleavage site for specific restriction enzymes and a molecular weight of less than $1.0 \times 10^7$, wherein said plasmid is selected from the group consisting of pSF765, pSF619 and pSF689.
2. The plasmid according to claim 1 which is pSF765.
3. The plasmid according to claim 1 which is pSF619.
4. The plasmid according to claim 1 which is pSF689.